United States Patent [19]

Ahlers et al.

[11] Patent Number: 5,430,110
[45] Date of Patent: Jul. 4, 1995

[54] POLYVINYLAMINE DERIVATIVES HAVING HYDROPHILIC CENTERS, PROCESSES FOR THEIR PREPARATION AND THE USE OF THE COMPOUNDS AS A MEDICAMENT, ACTIVE COMPOUND CARRIER AND FOODSTUFF AUXILIARY

[75] Inventors: Michael Ahlers, Mainz; Heiner Glombik, Hofheim am Taunus; Susanne Grabley, Königstein/Taunus; Ernold Granzer, Kelkheim/Taunus; Stefan Müllner, Hochheim; Axel Walch, Frankfurt am Main, all of Germany; Guan-Yu Xu, Shanghai, China

[73] Assignee: Hoechst Aktiengesellschaft, Germany

[21] Appl. No.: 95,623

[22] Filed: Jul. 21, 1993

[30] Foreign Application Priority Data

Jul. 22, 1992 [DE] Germany ............ 42 24 108.1

[51] Int. Cl.$^6$ .............................. C08F 8/30
[52] U.S. Cl. .................. 525/328.2; 525/328.4; 525/355; 525/359.1; 525/359.4; 525/374; 525/375; 525/384; 525/386
[58] Field of Search .................. 525/328.2, 328.4

[56] References Cited

U.S. PATENT DOCUMENTS

| | | |
|---|---|---|
| 3,558,581 | 1/1971 | Beermann et al. |
| 4,018,826 | 4/1977 | Gless, Jr. et al. |
| 4,362,711 | 12/1982 | Cerami |
| 4,421,602 | 12/1983 | Brunnmueller et al. |
| 4,943,676 | 7/1990 | Pinschmidt, Jr. et al. |
| 5,008,321 | 4/1991 | Hartmann et al. |
| 5,126,395 | 6/1992 | End et al. |

FOREIGN PATENT DOCUMENTS

| | | |
|---|---|---|
| 0262577 | 4/1988 | European Pat. Off. |
| 0162388 | 9/1989 | European Pat. Off. |
| 0339371 | 11/1989 | European Pat. Off. |
| 0379161 | 7/1990 | European Pat. Off. |
| 0404062 | 12/1990 | European Pat. Off. |
| 2006782A | 5/1989 | Spain |

OTHER PUBLICATIONS

Chem. Abstracts 112:119637j, Apr. 2, 1990 citing Jpn. Kokai 1 01,261,406.
Derwent 91-374734/38 citing DE 4007-311-A1.
Augurt, T. A.; Encyclopedia of Polym. & Technol; Vinylamine Polymers; vol. 14, Wiley & Son, N.Y. 1971, p. 251.
Fischer, Thomas, Dissertation, Marburg, Apr. 1992.
Storck, W. et al., Makromol, Chem., 110, 1967, No. 2589, pp. 207-221.
Ferruti, P., Adv. Polym. Sci. 58, 1984, pp. 55-92.
Bayer, E.; Makromol. Chem. 181, 1980, pp. 585-593.

*Primary Examiner*—Bernard Lipman
*Attorney, Agent, or Firm*—Barbara V. Maurer

[57] ABSTRACT

Polyvinylamine derivatives having hydrophilic centers, processes for their preparation and the use of the compounds as a medicament, active compound carrier and foodstuff auxiliary.

Polyvinylamine derivatives containing hydrophilic centers, of the formula I

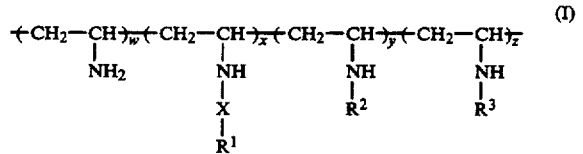

in which $R^1$, $R^2$, $R^3$, X, w, x, y and z have the meanings given, and a process for their preparation, and the use of these compounds as medicaments, active compound carriers and foodstuff auxiliaries are described. Highly pure polyvinylamines having the recurring unit of the formula Ia

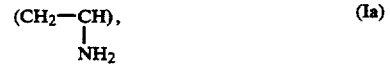

the preparation of which is likewise described, are used in particular as starting substances for the preparation.

4 Claims, 2 Drawing Sheets

POLYVINYLAMINE DERIVATIVES HAVING HYDROPHILIC CENTERS, PROCESSES FOR THEIR PREPARATION AND THE USE OF THE COMPOUNDS AS A MEDICAMENT, ACTIVE COMPOUND CARRIER AND FOODSTUFF AUXILIARY

The invention relates to soluble and insoluble nitrogen-containing vinyl polymers containing hydrophilic centers, their use as bile acid adsorber with the aim of reducing the blood cholesterol level, their use as an active compound carrier and as a foodstuff auxiliary and additive, and furthermore a process for the preparation of these compounds.

Bile acids have an important physiological function in fat digestion. As end products of cholesterol metabolism, they are synthesized in the liver, stored in the gall-bladder and released into the intestine, where they display their physiological action. The major proportion of bile acids secreted is recovered via the enterohepatic circulation (about 20–50 g/day). Suppression of this resorption reduces the bile acid pool in the liver and in this way causes an increased absorption of cholesterol from the blood circulation, as well as a stimulation in endogenous cholesterol synthesis. For this purpose, the number of hepatic LDL receptors on the membranes of the liver cells is increased, so that catabolism of the cholesterol-containing LDL particles is accelerated and the cholesterol content in the blood is reduced.

It is known that bile acids can be bonded to insoluble, basic, crosslinked polymers such as polyethyleneimines (cf., for example EP-A-0 379 161) or polyvinylimidazoles (cf. EP-B-0 162 388), and are therefore regarded as being suitable for treatment of diseases in which inhibition of the absorption of bile acid in the intestine, especially in the small intestine, appears to be desirable. For example, chologenic diarrhea following ileum resection or increased cholesterol blood levels are treated in this manner.

A very high daily dose is to De maintained, in particular, for the ion exchanger resins used as lipid-lowering agents, such as colestipol and colestyramine. For example, it is 12-24 g for colestyramine, 32 g in the highest instance, and 15-30 g for colestipol.

This high dosage and the unpleasant smell, taste and consistency makes patient compliance difficult.

Side effects of these ion exchanger resins are also to be attributed to the lack of selectivity (for example avitaminoses). For both preparations, a therapeutic importance has been reported in combination with other drugs which have a hypolipidemic action, such as fibrates, HMG-CoA reductase inhibitors and probucol (cf., for example, M. N. Cayen, Pharmac, Ther. 29, 187 (1985) and 8th International Symposium on Atherosclerosis, Rome, Oct. 9–13, 1988, Abstracts pages 544, 608, 710), the effects achieved also allowing treatment of severe cases of hyperlipidemia. It therefore seems important to discover substances which are suitable for the given action principle without having the disadvantages of the preparations currently used.

The following features of the preparations mentioned and in particular of colestipol are to be regarded as being worthy of improvement:

1. The high daily doses, which are due to a low bonding rate in isotonic solution and to partial re-release of the bile acid adsorbed.
2. The qualitative shift in the bile acid composition of bile with a decreasing trend for chenodeoxycholic acid and the associated increasing risk of cholelithiasis.
3. The absence of a suppressant action on the cholesterol metabolism of the intestinal bacteria.
4. The excessively high bonding rate of vitamins and drugs, which may necessitate a substitution requirement for these substances and blood level checks.
5. An inadequate purity and stability of the polymers (risk of splitting of ammonium groups from colestyramine).
6. Inadequate patient compliance because of a) the "sandy" consistency (colestyramine=hard gel polymer) and b) the unpleasant smell and taste.

Variations in the preparations used to date, such as, for example, introduction of spacers between ammonium groups and the polymer main chain in the case of colestyramine (EP-A-0 404 062), do not lead to a decisive reduction in the disadvantages described.

The object of the present invention was to provide compounds having a different polymer structure which bond bile acids to a high degree as a function of the concentration. These compounds moreover should not have the existing disadvantages of the exchanger resins used to date or should not have them to the same known extent.

The object is achieved and the deficiencies described are overcome with the highly water-absorbing polymers of the formula I and the highly pure polyvinylamines having the recurring unit of the formula Ia.

The invention therefore relates to polyvinylamines of the formula I.

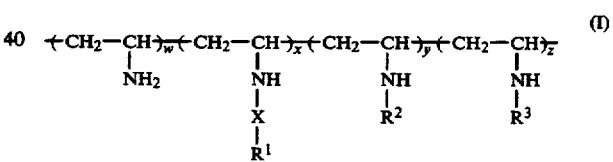

in which

R$^1$ is a substituent chosen from the group comprising:
1. —(CH$_2$)$_n$—CH$_3$, in which n is an integer from 3 to 21, branched alkyl having 3 to 21 carbon atoms or straight-chain or branched alkenyl having up to 21 carbon atoms,
2. cycloalkyl or cycloalkenyl having in each case 5–12 carbon atoms, or mono-, di- or trisubstituted cycloalkyl or cycloalkenyl having in each case 5–12 ring carbon atoms and
3. aryl, arylalkyl or arylalkenyl, in which the aryl radicals are mono- or polynuclear, can be mono- to trisubstituted and can contain heteroatoms, X is a single bond,
a bridge group or
a hydrophilic spacer for linking the radical R$^1$, R$^2$ is R$_A$—Y, R$_B$ or R$_C$, in which
Y is a bridge group or a spacer which allows R$_A$ to be linked to the polymer,
R$_A$ is a hydrophilic or amphiphilic substituent chosen from the group comprising:

1.

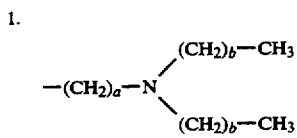

2.

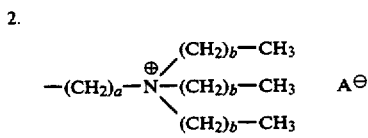

3.

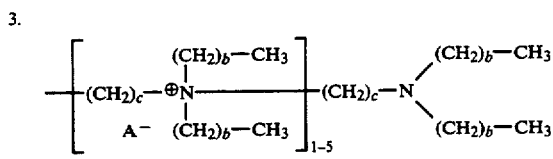

4. —(CH$_2$)$_c$—B, in which B is a pyrrolidinyl, piperidinyl or morpholinyl radical bonded via N, 5. —(CH$_2$)$_a$—D•A$^\oplus$, in which D• is pyridinium, pyrimidinium or imidazolinium,

6.

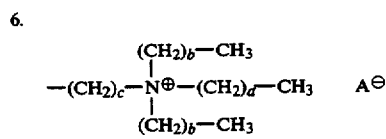

in which, for the substituents described under 1. to 6.,
a is an integer from 2 to 16,
b is zero, 1, 2 or 3,
c is an integer from 2 to 6,
d is an integer from 6 to 17 and
A is a physiologically tolerated anion,
R$_B$ 1. is a cholic acid bonded via the 3-α-OH or 24-COOH group directly or via a spacer, or
  2. is a tauro- or glycocholic acid which is bonded via the 3α-OH or tauro or glycofunction directly or via a spacer,
R$_c$ is a hydrophilic cyclic radical or a glucopyranuronic acid radical,
R$^3$ is a crosslinking group chosen from the group comprising:

1. —(CH$_2$)$_e$—,

2.

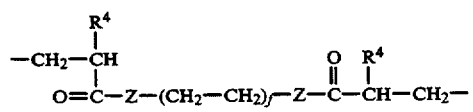

in which Z is oxygen or NH,

3.

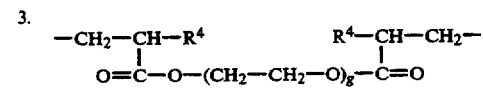

4. —(CH$_2$—CH$_2$—O)$_h$—CH$_2$—CH$_2$—,

5. W—(CH$_2$)$_g$—W, in which

W is a —$\overset{O}{\overset{\|}{C}}$—, —$\overset{O}{\overset{\|}{C}}$—NH— or —$\overset{O}{\overset{\|}{C}}$—O— group,

6.

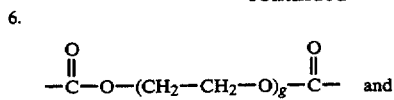 and

7.

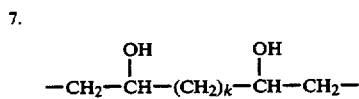

in which, in the groups described under 1. to 7.,
e is an integer from 3 to 12,
f is an integer from 1 to 6,
g is an integer from 1 to 8,
h is an integer from 1 to 7,
k is an integer from 4 to 8 and
R$^4$ is hydrogen or CR$_3$,
and in which
w is 0.1–0.995,
x is 0.0–0.8,
y is 0.01–0.8 and
z is zero or 0. 005–0.3, and w+x+y+z=1, and physiologically tolerated salts thereof.

The invention furthermore relates to highly pure polyvinylamines having the recurring unit of the formula 1a.

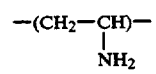

1a and physiologically tolerated salts thereof, obtainable by free radical polymerization of vinylformamide to give polyvinylformamide and subsequent hydrolysis.

Compounds of the formula I where n is zero are non-crosslinked and soluble, while the compounds where z is 0.005 to 0.3 are crosslinked and insoluble.

In the statements above and below: aryl is a mono- or polynuclear aromatic hydrocarbon radical having 6 to 14 carbon atoms, the aryl groups in the case of polynuclear radicals being fused with one another or bonded to one another via C—C bonds or via bridge members, such as —O—, —COO— or —CONH—. The term aryl furthermore also includes 5- to 14-membered heteroaryl having 1 heteroatom or 2 non-adjacent, identical or different heteroatoms chosen from the group comprising oxygen and nitrogen.

Aryl is, in particular, phenyl, arylalkyl is benzyl or phenylethyl and aralalkenyl is

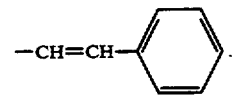

Examples of aromatic radicals having 1 or 2 heteroatoms are radicals of quinolinecarboxylic, benzimidazolecarboxylic, furancarboxylic, nicotinic and coumarilic acid.

The cycloalkyl and cycloalkenyl radicals are optionally mono-, di- or trisubstituted by hydroxyl, (C$_1$-C$_6$)-alkyl and/or (C$_1$-C$_6$)-alkoxy radicals, and in the case of polysubstitution, the substituents are identical or different. Corresponding statements also apply to the substituents on aryl; a possible radical is, for example, a triethylbenzoic acid radical.

The bridge member X is

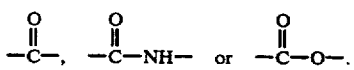

The hydrophilic spacer X is a radical of the formula

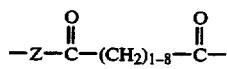

where Z is oxygen or NH, and in which, in the case of 3–8 methylene groups, a central $CH_2$ group can be replaced by oxygen, and in which the alkylene chain can be substituted by 1 to 4 hydroxyl groups, or a radical of the formula

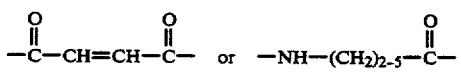

$R^1$—X is, for example, a radical of the formula

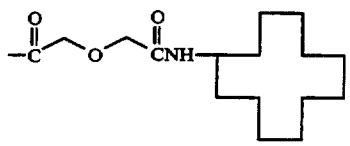

The bridge member Y is

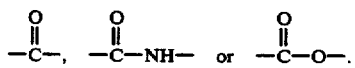

The spacer Y is a radical of the formula

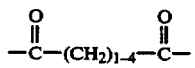

in which, in the case of 3–4 methylene groups, a central $CH_2$ group can be replaced by oxygen. An example of $R^2$ as $R_B$ is the radical of the formula

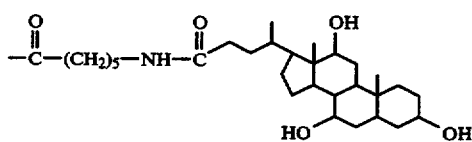

A hydrophilic cyclic radical $R_c$ is a cyclodextrin radical or a functionalized 7- to 18-membered carbon-containing azamacrocyclic radical having 2 to 4 nitrogen atoms and optionally 2, 3 or 4 oxygen atoms, which are separated by ethylene groups, such as, for example, 1,4,7-triazacyclononane, a cyclene or cyclam radical or 1,4-diaza-18 crown 6.

The polyvinylamines of the formula I where z is zero and the highly pure polyvinylamines having the recurring unit of the formula Ia are linear.

As is customary in polymer chemistry, the molecular portions occurring w, x, y and z times shown in the formula I are randomly distributed over the entire polymer or can be concentrated in blocks on the basis of adjacent group effects, especially in the case of hydrophobic substituents.

The radical $R^1$ is preferably hydrophobic.

If b occurs more than once in a structure, b is identical or different. c, R4 and W are always identical in a structure. Highly pure polyvinylamine (PVAm) or PVAm salt is understood as meaning polymers having a molecular weight of 10,000 to 1,000,000 D which contain no residual monomers, no free initiator constituents and no cocomponents detectably in the polymer.

Vinylamine polymers and their preparation have already been described.

Crosslinked PVAm prepared from isopropyl N-vinylcarbamate have been described as an anion exchanger (Storck, W. and Manecke G., Makromol. Chem. 110, 207 (1967)). U.S. Pat. No. 4,018,826 describes the preparation of polyvinylamine(PVAm) from polyvinylacetonitrile, and U.S. Pat. No. 4,943,676 describes partial thermolysis of polyvinylformamide to give polyvinylamine. Copolymers of vinylformamide and vinylamine prepared by polymerization of vinylformamide and subsequent partial hydrolysis are described in EP-B-0 071 050 and DE-A-40 07 310. EP-A-0 262 577 describes a homopolymer of at least $10^{+6}$ D MW (molecular weight), which "chiefly" comprises polyvinylamine units and was prepared by inverse emulsion polymerization.

EP-A-0 374 646 relates to the preparation of water-in-oil emulsions from polyvinylamine.

In accordance with the information in the abovementioned publications, polyvinylamines are suitable for industrial uses in the non-medical field, for example as flocculating agents in papermaking, thickeners in tertiary crude oil production, additives for engine oils and as filter membranes.

Spanish Patent No. 2 006 782 describes the preparation of a specific ion exchanger from vinylamine, epichlorohydrin and chloroammonium-glycidine. This ion exchanger is said to have cholesterol-lowering properties. There is no information on its pharmacological action. With knowledge of the publications by T. A. Augurt in Encyclopedia of Polymer Science and Technology, Vol. 14; Wiley & Sons, NY, 1971, page 251; P. Ferruti et al., Adv. Polym. Sci, 58, 55–92 (1984) and Bayer E. et al. Makromol. Chem. 181, 585 (1980), however, the synthesis could not be reconstructed.

The dissertation by Thomas Fischer (Marburg 1992) relates to bile acid adsorbers based on aliphatic polyamines. The polyvinylamines described are free from additional hydrophilic centers.

Finally, U.S. Pat. No. 4,362,711 describes vesicles of a polymer matrix filled with a solution, which can contain polyvinylamine hydrochloride as a constituent, as a bile acid sequestrant without mentioning the activity.

It has now been found that the introduction of additional hydrophilic centers in particular leads to compounds having a good action.

On the basis of the known prior art, PVAm is obtained by polymerization of vinylformamide with subsequent hydrolysis to give polyvinylamine, and if appropriate a polymer-analogous reaction. To avoid intolerances on the basis of possibly toxic, low molecular weight constituents, such as residues of initiator and monomers, antioxidants, regulators and by-products, it is necessary for use in the medicaments sector for these to be removed from the polymer without trace, which under certain circumstances is very expensive or cannot be carried out at all in practice.

A route has now been found for preparing the base polymer having the recurring unit of the formula Ia in a highly pure form. An essential prerequisite for the use of the compounds in the pharmaceuticals sector is therefore met.

The invention therefore also relates to a process for the preparation of highly pure polyvinylamines having the recurring unit of the formula Ia, which comprises preparing polyvinylformamide (homopolymer) by free radical polymerization of vinylformamide and subsequently hydrolyzing the product, highly pure polyvinylamine being formed. The polyvinylformamide intermediately formed is expediently subjected to purification by ultrafiltration and freeze drying before the hydrolysis.

The invention furthermore relates to a process for the preparation of polyvinylamines of the formula I, which comprises introducing the functional groups $R^1$—X, $R^2$ and/or $R^3$ into polyvinylamines having the recurring unit of the formula I by methods customary in polymer chemistry.

The highly pure PVAm having the recurring unit of the formula Ia prepared by the process according to the invention is preferably employed in the above process.

Compounds of the formula I comprise, individually or in combination, the following structural elements: polymer main chain, hydrophilic, cationic, amphiphilic and hydrophobic substituents and crosslinking group. The compounds are synthesized by polymer-analogous reactions, preferably on PVAm of the formula Ia prepared according to the invention. For this, the hydrochloride salt or the free base form of the polymer is alkylated, acylated, substituted by addition of the Michael type or on isocyanates or reacted with epoxides.

PVAm is partly alkylated by customary methods using agents of the formula R—M, in which M is chlorine, bromine, iodine, $CH_3$—$SO_2$—O or tosyl and R is such that polymers as described in formula I are formed, in water or in a mixture with a water-miscible organic solvent, such as dioxane, DMF, formamide and the like, in a homogeneous phase or as a phase boundary reaction with phase transfer agents, such as sodium dodecyl sulfate or cetyltrimethylammoniumbromide, with or without addition of auxiliary bases, such as NaOH, KOH, triethylamine or pyridine. Analogously, PVAm can be reacted by acylation with the corresponding acid chlorides, bromides or anhydrides. Acylation with active esters such as paranitrophenyl-carboxylic acid esters is particularly successful in methanol.

Compounds containing suitable functional groups, such as, for example, benzyl chloride, bromomethylbenzene, cinnamic and hydroxycinnamic acid, naphthylacetic acid, N-(ω-bromohexyl)carbazole, furancarboxylic acid and nicotinic acid, can be used to prepare polyvinylamine derivatives having aromatic substituents.

Medium- to long-chain n-alkyl and branched and cyclic alkyl and alkenyl halides, mesylates and tosylates are employed, for example, for introduction of substituents $R^1$, which preferably have a hydrophobic character, by alkylation. Butyl, hexyl, dodecyl and hexadecyl bromides are preferred. Hexanoyl, decanoyl, lauroyl, stearoyl chloride are used for the acylation. The hydrophobic radical $R^1$ can be detached from the polymer main chain by hydrophilic spacers X—preferably by using succinic or diglycolic anhydride.

Halides of alkyl- or hydroxyalkylamines and corresponding ammonium salts, such as, for example, the hydrochlorides of dimethylaminoethyl chloride, dimethylaminopropyl chloride, diethylamino-ethyl, -propyl and -hexyl chloride and bromopropylpyridinium chloride, are preferably used for introduction of hydrophilic substituents $R^2$. If an anion $A^\ominus$ occurs in $R^2$, this is a physiologically tolerated anion, such as Cl⁻, Br⁻, $HCO_3$, malonate, citrate, ascorbate and the like, preferably Cl⁻. ω-Bromododecyltriethylammoniumchloride and ω-mesylethyldimethyldodecylammonium chloride are preferably used for introduction of amphiphilic substituents $R^2$, so that optionally either the ammonium center or the hydrophobic alkyl part is linked directly to the polymer main chain. To utilize a template effect, bile acids are linked to PVAm derivatives directly or via a spacer.

Substitution for the derivatives prepared in a polymer-analogous manner is effected with up to 80%, preferably 5–40%, per radical $R^1$ or $R^1X$ and for $R^2$ with 1–80%, preferably 5–40%, but not more than 90% in total, so that at least 10% of the amino groups of the PVAm are present in the free form or partly as the physiologically tolerated salt.

Both hydrophilic and hydrophobic linking agents are employed as crosslinking agents, such as, for example, dibromohexane, dibromopropane, diepoxypropyl ether, epichlorohydrin, adipic acid dichloride, triethylene glycol ditosylate and ethyldiacrylamide.

The degree of crosslinking varies from 0.5 to 30%, preferably from 3 to 15%. The degree of swelling in water can be adjusted from 2 ml/g to 1 l/g by the extent of crosslinking. A degree of crosslinking of 10–300 ml/g, in particular 50–200 ml/g, is particularly preferred.

The soft gel polymers are worked up by direct and inverse precipitation with a precipitating agent, preferably acetone, and by ultrafiltration and freeze drying.

The base polymer PVAm is used as the starting material for preparation of the functional polymers of the formula I, it being necessary for this base polymer to meet the prerequisites for medical use. PVAm is therefore prepared by the process according to the invention, which allows a homopolyvinylamine, which contains no further cocomponents in polymer and is free from low molecular weight impurities, to be obtained.

For this, for example, vinylformamide is polymerized in 14% strength aqueous solution With 0.5 mol % of the free radical initiator 4,4'-azocyanopentanoic acid (ACPA) at 70° C. for 8 hours. A polyvinylformamide having a viscosity of 1.74 dl/g is obtained with a conversion of 99.8%. This polymer is purified by ultrafiltration (10,000 D membrane) such that residual monomer or free initiator constituents are no longer detectable (less than 1 ppb in 1% strength solution).

Conditions: membrane cassettes with exclusion limit of 10,000 D MW, Minisette from Filtron, for example once with 3×101 of $H_2O$/100 g of polymer and once with 3×101 of $H_2O$/20 g of polymer.

The amounts of water required can be purified, if necessary by active charcoal, and used several times.

Determination of vinylformamide by means of HPLC:

Column: ®LiChrosorb Si 60 (5 μm)
Flow rate: 0.55 ml/minute
Pressure: 360 psi
Detector: UV, 225 nm
Retention time: 7.2 minutes.

Before the determination of vinylformamide in the polyvinylformamide, the polymer solution is passed over a purified preliminary column (silica gel 60). Calibration solutions are treated in an identical manner to the polymer solution.

BRIEF DESCRIPTION OF THE DRAWINGS

For the HPLC elution diagram see FIG. 1 (PVAm according to Example 1).

For the calibration for the HPLC determination of vinylformamide, see FIG. 2.

Figure 1:
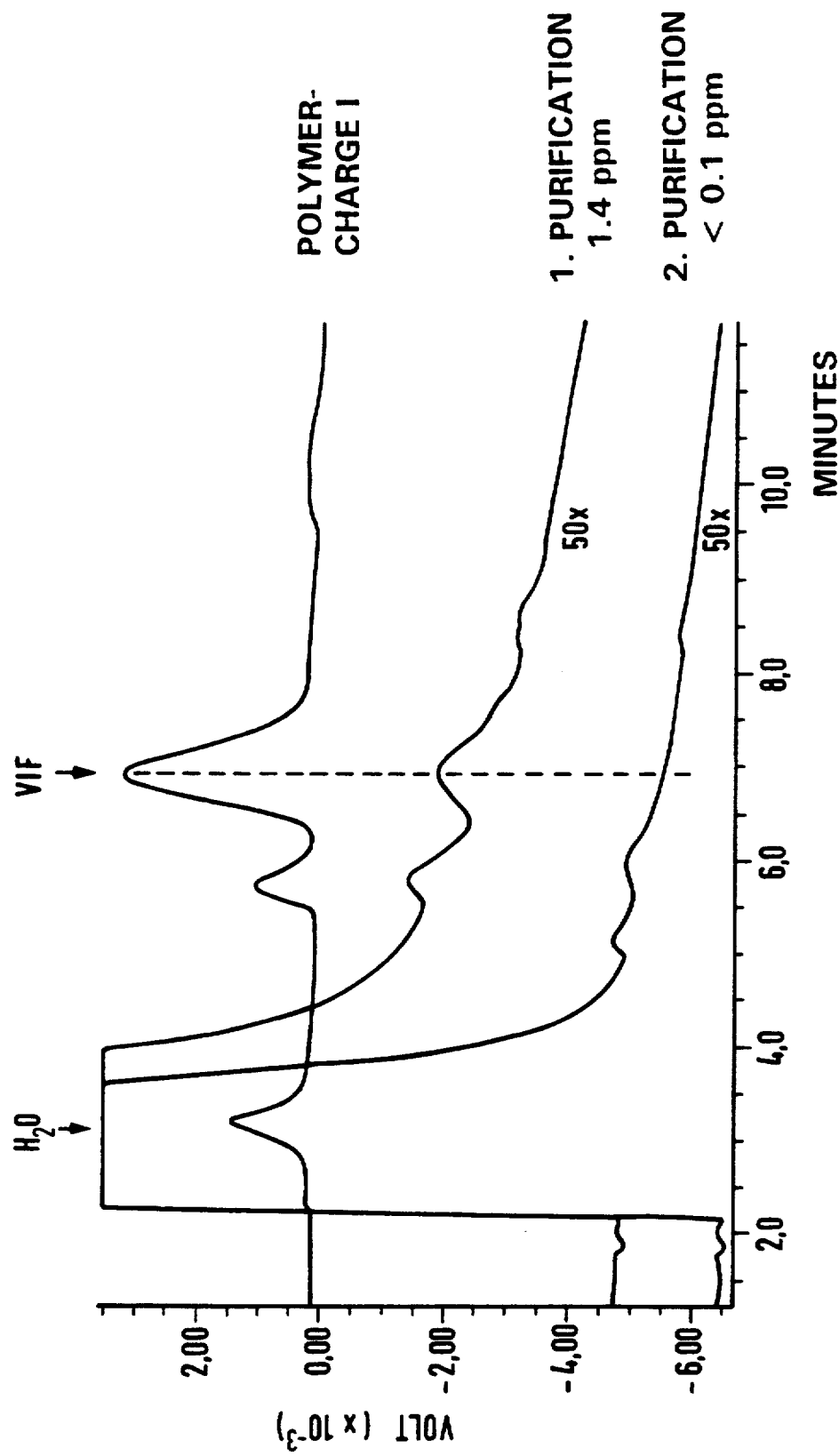
Figure 2:
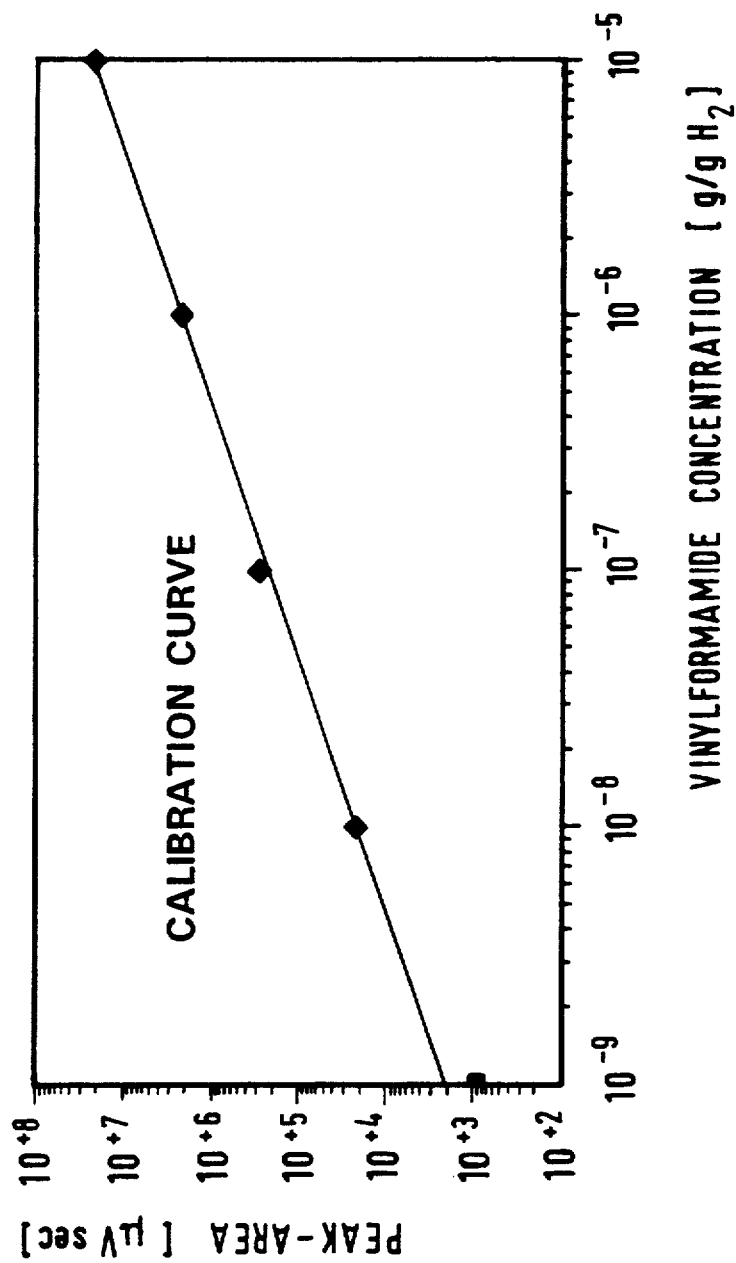

A polymer of viscosity 2.48 dl/g is obtained with 0.25 mol % of ACPA, while a viscosity of 0.31 dl/g is reached by precipitation polymerization in isopropanol. The molecular weight can be adjusted by the customary method (choice of the parameters of initiator and monomer concentration and temperature).

Polyvinylformamide of very high molecular weight (>1,000,000 D) was prepared and hydrolyzed to PVAm, but this has a weaker action in respect of bile acid adsorption than derivatives of low molecular weight (for example 75,000 D). It has been found that in the case of pure PVAm, PVAm derivatives and crosslinked secondary products thereof, in each case the preparations having a lower MW of the starting polymer have better bile acid adsorption values than those of high molecular weight. The compounds prepared from a starting polymer with a molecular weight which is not too high (less than 1,000,000, for example 10,000 to 500,000 D) are therefore preferred.

To prepare PVAm which is free from cocomponents, ⅓ the volume (v/v) of a strong acid, for example concentrated HCl, is added to the aqueous polyvinylformamide solution and the mixture is heated under reflux for 2 hours. Thereafter, about ⅔ the volume (v/v) of acid are added over a period of 6 hours, while heating, such that the polymer remains dissolved. Only after the hydrolysis does PVAm precipitate on cooling, so that it can be separated off from the reaction solution. Formic acid and the excess hydrochloride are removed by ultrafiltration.

Another possibility for the preparation of insoluble PVAm formulations is ionic complexing of the amino-containing polymers with di-, tri- and tetraacids and oligo- and polyacids to give polyelectrolyte complexes (PEC). For this, a dilute solution of the acid is usually initially introduced into the reaction vessel and the solution of the polybase is added dropwise such that fine gel droplets which can be separated are formed.

The invention furthermore relates to bile acid adsorbents of the formula I and bile acid adsorbents having the recurring unit of the formula Ia, which, if appropriate in the form of salts, are particularly suitable for treatment of cases of hyperlipidemia, and to the preparation of such medicaments.

To prepare highly active bile acid adsorbents, compounds of the general formula I and highly pure PVAm having the recurring unit of the formula Ia which, compared with the adsorbents used at present, have a higher bonding capacity were synthesized using a) polymers having recurring units of low molecular weight,
b) more effective ion exchanger groups and
c) formulations having a large active surface area.

An improved selectivity can be achieved by utilizing either electrostatic or hydrophobic interactions as well as specific network structures.

The usual dosage of the bile acid adsorbers used to date for treatment of hypercholesterolemia can be reduced considerably by using the vinyl polymers. The problem of dosage and compliance thereby arise to a lesser extent. In addition, compliance is also improved by the fact that the compounds have a soft gel character and are of neutral taste and smell, so that no taste and smell compensators are required.

The effectiveness of the active compounds described can be increased by specific microformulations. For this, the compounds are converted into microparticles by means of various techniques. In the case of soluble compounds, this is possible by spray drying, freeze drying and emulsion processes. Soluble and insoluble compounds can also be micronized mechanically. The microparticles are distinguished by the fact that the active compound is substituted over a very large adsorptive surface area.

Crosslinked microparticles can thus be prepared from the compounds of the formula I inter alia, by spraying a 4% strength aqueous solution of basic PVAm or non-crosslinked derivatives thereof at 170° C. The nano- and microparticles obtained are suspended in isopropanol or dichloroethane with 0.3–0.5% of dibromohexane and the suspension is incubated at 70°–80° C. for 8 hours. The particles are insoluble in water, but swell, their diameter increasing 1½- to 5-fold.

One advantage of the compounds of the formula I and the PVAm having the recurring unit of the formula Ia is that film-coated tablets can be prepared very easily from these compounds. In vitro, these exhibit the same activity as the compounds in powder form. Per 250 mg of active compound, for example, they comprise only 40 mg of pharmaceutically customary auxiliaries.

The reduction in serum cholesterol level to be achieved with the compounds can be improved further by simultaneous use of other lipid-lowering agents which do not have a systemic action or have a systemic action (for example HMG-CoA reductase inhibitors) in the context of a combination therapy.

Since the compounds according to the invention interrupt the enterohepatic circulation, they are suitable as an antidote in the event of oral toxification.

The compounds of the formula I where z=0.005 to 0.3 furthermore can be employed as satiation promoters because of their water uptake capacity.

Since the compounds of the formula I according to the invention and PVAm having the recurring unit 1a are readily swellable and bond acids, they can be employed as antacids for the treatment of excessive production of gastric acid, and can therefore be used as agents against gastritis and ulcus ventriculi or duodeni.

On the basis of their interaction with cholesterol, the compounds are capable of adsorbing the cholesterol consumed with food. The content of cholesterol in food is therefore bonded immediately and is not adsorbed by the body.

The compounds of the formula I are furthermore also suitable as foodstuff auxiliaries. Thus, for example, cholesterol is adsorbed from milk or egg constituents. The resulting foodstuffs are distinguished by a reduced cholesterol content.

Compounds of the formula I or highly pure PVAm having the recurring unit of the formula Ia are suitable as muco-adhesive transportation systems for active compounds. They form highly hydratable polymer matrices which have groups which form hydrogen bridges and cationic groups, display a high flexibility of the polymer chain and can be additionally substituted by hydrophobic units. The compounds are therefore capable of increasing the residence time of a bonded or adsorbed active compound in the stomach or small intestine. They are adsorbed as active compound carriers onto the mucosal layer of the gastro-intestinal wall, the positively charged groups of the polymers interacting with the negatively charged groups of the terminal sialic acid of the mucin molecules in order thus to cause delayed transportation of the active compounds through the gastrointestinal tract. At the same time, the absorption of the active compound is improved by the nature of the interaction.

In vitro test

The bonding capacity and selectivity are tested in an in vitro test. A bovine bile assay is used here. For this, 5 mg of polymer sample are dissolved in 2 ml of test solution and the solution is incubated at 37° C. for 24 hours. The test solution comprises bovine bile, diluted 1:10 with PBS buffer, pH 6.5. Evaluation is by means of thin-layer chromatography and HPLC. Cuemid is used as the reference. The results are summarized in Table 1.

TABLE 1

Bile acid adsorption in vitro (bovine bile assay)

| Example | Bile acid adsorption (%) | |
|---|---|---|
| | Taurocholate | Glycocholate |
| 4 | 69 | 72 |
| 5 | 64 | 68 |
| 6 | 65 | 71 |
| 7 | 63 | 58 |
| 8 | 58 | 60 |
| 9a | 48 | 50 |
| b | 44 | 44 |
| c | 60 | 54 |
| d | 36 | 38 |
| e | 36 | 38 |
| f | 32 | 30 |
| 10 | 42 | 20 |
| 11 | 68 | 65 |
| 12 | 63 | 63 |
| 13 | 54 | 51 |
| Colestyramine | 38 | 24 |

In vivo test

The action of four preparations in respsect of a reduction in serum cholesterol level was tested on rabbits fed with cholesterol.

For this, after a preliminary feeding period (to raise the cholesterol level) the cholesterol level was determined (initial value). 2% strength cholesterol-containing food and the preparations in concentrations of 12.5–50 mg/kg (or 100–500 mg for colestyramine) were fed to randomized test groups of 5 animals each for 4 weeks. The change in serum cholesterol compared with the initial value is shown for each preparation and for colestyramine as the comparison substance in Table 2.

TABLE 2

Change in the total cholesterol of rabbits fed with 0.2% of cholesterol

| Preparations | Dosage | Change in serum cholesterol compared with the initial value |
|---|---|---|
| Control ®Tylose | 1% | +4 mmol/l |
| Example 5 | 50 mg/kg | −2.5 mmol/l |
| Example 6 | 50 mg/kg | −1 mmol/l |
| Example 7 | 50 mg/kg | +0.5 mmol/l |
| Example 8 | 50 mg/kg | −0.4 mmol/l |
| Colestyramine | 500 mg/kg | −0.3 mmol/l |

Example 1

Vinylamine homopolymer for pharmaceutical quality MW: - 380,000 D 1.8 l of deionized water are heated to 60° C., degassed and flushed with $N_2$. 300 g of vinylformamide, 3 ml of concentrated $NH_4OH$ and 6 g of ACPA are added, and the entire mixture is stirred at 70° C. for 8 hours. The monomer conversion is monitored by $I_2$ titration, and is 99.8% after 8 hours.

The solution is diluted 4 times with water to in each case 20 l and concentrated in each case 4 times to 2.5 l by means of ultrafiltration (5×10 K Minisette from Filtron), and then freeze dried. A purely white product having a residual monomer content of 1.4 ppm is obtained.

50 g of the polymer are dissolved in water again, the solution is diluted to 10 l and ultrafiltered 4 times and the product is then freeze dried.

The residual monomer content is below the detection limit of the HPLC method (<0.1 ppm) and GC-MS. Viscosity [$\eta$] in 0.5% strength NaCl: 1.74 dl/g.

100 g of polyvinylformamide are dissolved in 800 ml of $H_2O$, 270 ml of concentrated HCl are added and the mixture is heated under reflux for 2 hours. 270 ml of concentrated HCl are added. The mixture is heated under reflux for 4 hours and, after addition of a further 270 ml of concentrated HCl, is heated at 60° C. for 2 hours. The hydrochloric acid is decanted off at room temperature, the polymer is dissolved in $H_2O$ and the pH is brought to 4 with NaOH. The product is ultrafiltered 4 times with in each case 20 l and then freeze dried. According to $^1H$-300 MHz-NMR, the polymer no longer contains formamide groups (no peak between 8 and 8.5 ppm), i.e. the content is below the detection limit (<0.05%).

The free base form of the PVAm can be obtained from the above polymer using alkali metal hydroxide solution and subsequent dialysis and freeze drying by using ion exchanger resins.

Example 2

Vinylamine homopolymer for pharmaceutical quality MW: - 75,000 D 100 g of vinylformamide, 0.5 ml of concentrated $NH_3$ and 1.5 g of ACPA are added to 500 ml isopropanol. The mixture is stirred at 65° C. for 6 hours. The polymer is filtered off with suction, dried in vacuo, dissolved in water and ultrafiltered as described in Example 1.

50 g of polyvinylformamide are dissolved in 400 ml of $H_2O$, and concentrated NaOH solution (83 g) are added at 50° C. such that the polymer does not precipitate. The mixture is stirred at 70° C. for 7 hours. The polymer is precipitated in acetone, dissolved in water and further purified by ultrafiltration and freeze drying as described in Example 1.

Example 3

0.165 g of PVAm (75,000 D from Example 2) are dissolved in 3 ml of methanol, and 0.4 g of cholic acid ω-amidocaproic acid p-nitrophenyl ester in 10 ml of dimethyl sulfoxide is added. Three drops of triethylamine are added and the mixture is stirred at room temperature for 1 hour. The product is precipitated in ethyl acetate and dissolved in methanol/$H_2O$, the pH is brought to 4 and the product is precipitated again in ethyl acetate. The polymer is filtered off with suction and dried in vacuo.

Yield: 310 mg Degree of substitution: 12%

Example 4

2 g of PVAm (Example 1, basic form) are dissolved in 80 ml of H$_2$O, 4.5 g of 6-bromohexylpyrimidinium bromide and 560 mg of NaOH are added, and the mixture is stirred at 90° C. for 9 hours.

For working up, the batch is acidified with 1N HCl (pH 1) and precipitated inversely with acetone. The product is dissolved in H$_2$O, the solution is titrated with NaOH to pH 4 and the product is precipitated again with acetone. After a further precipitation in acetone, the resulting product is freeze dried from H$_2$O.

Yield: 4 g

Example 5

360 g of PVAm×HCl (24% of Cl) are dissolved in 5 l of H$_2$O. After the pH has been brought to 10, 323 g of 6-bromohexylpyridinium bromide and 72 g of NaOH are added. The mixture is stirred under N$_2$ at 90° C. for 10 hours. Thereafter, it is neutralized with hydrochloric acid and ultrafiltered with 30 l of H$_2$O (cut off: 10,000 D).

Degree of substitution according to NMR: 15.7%.

The batch (4 l) is brought to pH 10 with NaOH, and 69 g of 1,6-dibromohexane and 22 g of NaOH are added. The mixture is heated to 90° C. under N$_2$, with very rapid stirring. After about 1½ hours, gel formation starts. The mixture is stirred at 90° C. for a further 4½ hours. For working up, the batch is acidified with 2 l of 2N hydrochloric acid and the product is precipitated inversely with 10 l of acetone. The bromide/chloride exchange is carried out by swelling the polymer in 2N hydrochloric acid. Thereafter, the product is again precipitated inversely with acetone and taken up in 8 l of H$_2$O, and the pH is brought to 5 with dilute sodium hydroxide solution. After precipitation in acetone, the product is dried in vacuo at 50° C.

Yield: 460 g.

Example 6

140 g of PVAm×HCl are dissolved in 4 l of H$_2$O and the pH is brought to 11 with NaOH. After addition of 32 g of dimethylaminoethyl chloride hydrochloride and 18 g of NaOH, the mixture is stirred under N$_2$ at 85° C. for 9 hours.

The pH is brought to 1 with hydrochloric acid and the batch is precipitated with acetone. The product is dissolved in H$_2$O, the pH is brought to 5 and the product is ultrafiltered and freeze dried.

Degree of substitution: 6% Yield: 150 g.

Example 7

110 g of PVAm from Example 1 are dissolved in 4 l of H$_2$O, and 36.8 g of dimethylaminoethyl chloride hydrochloride and 25.6 g of NaOH (in 200 ml of H$_2$O) are added. The mixture is heated at 90° C. for 9 hours. 80 g of dibromohexane are added, while stirring rapidly. After 2 hours, the solution changes into a gel. The temperature is kept at 85°–90° C. for 9 hours. The batch is diluted with 3 parts of acetone (v/v) and the gel is extracted. The solution is decanted off and the residue is extracted by stirring in further acetone. The product is swollen in water/ethanol, the pH is initially brought to 1, and the polymer is precipitated with acetone and swollen again in water at pH 4. After a further precipitation with acetone, the product is finally dried in vacuo at 50° C.

Example 8

100 g of PVAm×HCl are dissolved in 2.5 l of H$_2$O and the pH is brought to 11 with NaOH. After addition of 87 g of (3-bromopropyl)-trimethylammonium chloride and 27 g of NaOH, the mixture is boiled under reflux under N$_2$ for 17 hours. Working up is carried out analogously to Example 6 by acidification, precipitation in acetone and ultrafiltration.

Degree of substitution: 20%. Yield: 99 g.

Example 9 a, b, c, d, e, f 2 g of PVAm×HCl (33 mmol) are initially introduced into 70 ml of H$_2$O and the pH is brought to 10 with 10 ml of sodium hydroxide solution. In 6 batches (a–f), 0.26 g; 0.64 g; 1.28 g; 1.92 g; 2.56 g and 3.19 g of 12-bromododecyltrimethylammonium bromide are dissolved in 10 ml of H$_2$O with 1.1 times the particular molar amount of NaOH, and the solutions are added dropwise. The batches are stirred at 80° C. for 7 hours. Batches a, b and c are worked up analogously to Example 4; for working up batches d, e and f, these are freeze dried. The product is taken up in methanol/H$_2$O and precipitated in acetone/diisopropyl ether 3:2. The precipitation is repeated at pH 1 and pH 4. The batches are freeze dried from H$_2$O.

9a) Degree of substitution: 2% Yield: 58%
b) Degree of substitution: 5% Yield: 54%
c) Degree of substitution: 8% Yield: 40%
d) Degree of substitution: 12% Yield: 88%
e) Degree of substitution: 19% Yield: 85%
f) Degree of substitution: 25% Yield: 91%

Example 10

10 ml of an aqueous solution of polyacrylic acid (Polyscience, 450 kD) are initially introduced into the reaction vessel in a concentration of 1 mg/ml. 10 ml of the compound from Example 1 are added dropwise in a concentration of 1 mg/ml by means of a cannula (diameter 0.6 mm). A gel is formed, which is freeze dried; according to analysis, the gel comprises 50% of the polybase of Example 1.

Example 11

1 g of PVAm (Example 1, salt-free form) is dissolved in 40 ml of H$_2$O, 588 mg of benzyl chloride are added and the mixture is stirred at 90° C. for 8 hours. After addition of 2.25 g of 6-bromohexylpyridinium bromide and 470 mg of NaOH, the mixture is stirred at 90° C. for 8 hours. Working up is carried out analogously to Example 4.

Degree of substitution: 18% benzyl, 28% hexylpyridinium Yield: 0.76 g

Example 12

1 g of PVAm (Example 1, salt-free form) is dissolved in 40 ml of H$_2$O, 588 mg of benzyl chloride are added and the mixture is stirred at 90° C. for 8 hours. After addition of 1.96 g of 3-bromopropylpyridinium bromide and 470 mg of NaOH, the mixture is stirred at 90° C. for 8 hours. For working up, 23 ml of the solution are treated as described in Example 4.

Substitution: 18% benzyl, 8% propylpyridinium ½ yield: 0.66 g

Example 13

430 mg of dibromohexane and 150 mg of NaOH are added to 23 ml of the reaction solution from Example 12 and the mixture is stirred at 90° C. for 8 hours. Working up is carried out analogously to Example 7.

Yield: 0.96 g

Example 14

1.35 g of trimethyldodecylammonium chloride-substituted PVAm - 0.25 (obtained as the free amine from Example 9f by means of the ion exchanger Amberlite 400) are dissolved in 60 ml of ethanol/H$_2$O 1:1, and 1.8 g of p-nitrophenyl caproate in 20 ml of ethanol are added. The mixture is stirred at room temperature for 2 hours and at 40° C. for ½ hour. The pH is brought to 6 with hydrochloric acid, the ethanol is evaporated off in a rotary evaporator and the aqueous phase is freeze dried. The polymer is precipitated in ether from ethanol/isopropanol 1:1, dissolved in H$_2$O, dialyzed (cutoff: 15,000) and freeze dried.

Yield: 1.5 g.

We claim:

1. A polyvinylamine derivative containing hydrophilic centers, of the formula I

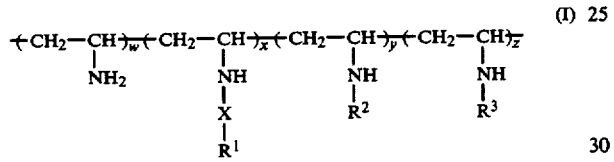

in which

R$^1$ is a substituent chosen from the group comprising:
1. —(CH$_2$)$_n$—CH$_3$, in which n is an integer from 3 to 21, branched alkyl having 3 to 21 carbon atoms or straight-chain or branched alkenyl having up to 21 carbon atoms,
2. cycloalkyl or cycloalkenyl having in each case 5-12 carbon atoms, or mono-, di- or trisubstituted cycloalkyl or cycloalkenyl having in each case 5-12 ring carbon atoms and
3. aryl, arylalkyl or arylalkenyl, in which the aryl radicals are mono- or polynuclear, can be mono- to trisubstituted and can contain heteroatoms, X is a single bond,
a bridge group or
a hydrophilic spacer for linking the hydrophobic radical R$^1$, R$^2$ is R$_A$—Y, R$_B$ or R$_C$, in which
Y is a bridge group or a spacer which allows R$_A$ to be linked to the polymer,
R$_A$ is a hydrophilic or amphiphilic substituent chosen from the group comprising:

1. 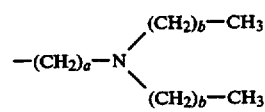

2. 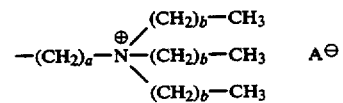

3. 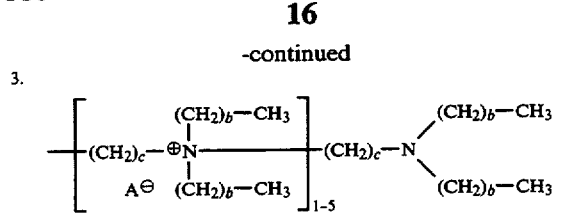

4. —(CH$_2$)$_c$—B, in which B is a pyrrolidinyl, piperidinyl or morpholinyl radical bonded via N,
5. —(CH$_2$)$_a$—D•A$^\oplus$, in which D• is pyridinium, pyrimidinium or imidazolinium, 6. 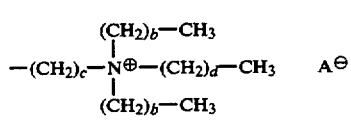

in which, for the substituents described under 1. to 6.,
a is an integer from 2 to 16,
b is zero, 1, 2 or 3,
c is an integer from 2 to 6,
d is an integer from 6 to 17 and
A is a physiologically tolerated anion, R$_B$ 1. is a cholic acid bonded via the 3-α-OH or 24-COOH group directly or via a spacer, or
2. is a tauro- or glycocholic acid which is bonded via the 3α-OH or tauro or glyco function directly or via a spacer, R$_C$ is a hydrophilic cyclic radical or a glucopyranuronic acid radical, R$^3$ is a crosslinking group chosen from the group comprising:

1. —(CH$_2$)$_e$—,

2. 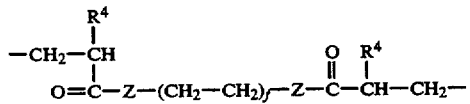

in which Z is oxygen or NH,

3. 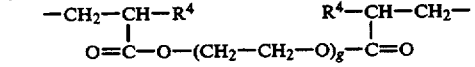

4. 

5. W—(CH$_2$)$_g$—W, in which
W is a  group,

6. 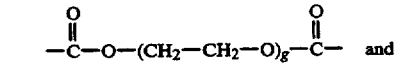 and

7. 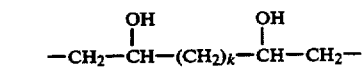

in which, in the groups described under 1. to 7., e is an integer from 3 to 12, f is an integer from 1 to 6,
g is an integer from 1 to 8,
h is an integer from 1 to 7,
k is an integer from 4 to 8 and
$R^4$ is hydrogen or $CH_3$,
and in which
w is 0.1–0.995,
x is 0.0–0.8,
y is 0.01–0.8 and
z is zero or 0.005–0.3, and w+x+y+z=1, or a physiologically tolerated salt thereof.

2. A polyvinylamine derivative as claimed in claim 1, in which z is zero.

3. A polyvinylamine derivative as claimed in claim 1, in which z is 0.005 to 0.3.

4. A medicament comprising a compound as claimed in claim 1.

* * * * *